United States Patent [19]

Purcell et al.

[11] 4,361,700
[45] Nov. 30, 1982

[54] PYRIDOPYRIMIDINONE DERIVATIVES

[75] Inventors: William P. Purcell; Richard D. Gilliom; Harlie A. Parish, Jr., all of Memphis, Tenn.

[73] Assignee: James S. Waldron, Washington, D.C.

[21] Appl. No.: 151,566

[22] Filed: May 20, 1980

[51] Int. Cl.³ .......................................... C07D 487/04
[52] U.S. Cl. .................................... 544/279; 544/10; 544/48; 544/105; 544/257
[58] Field of Search .................... 544/257, 279, 10, 48

[56] References Cited
PUBLICATIONS

Osselaere et al., Eur. J. Med. Chem.-Chim. Ther. 1974, 9 (3), 305-309, 310-312.

Primary Examiner—Paul M. Coughlan, Jr.
Attorney, Agent, or Firm—Fidelman, Wolffe & Waldron

[57] ABSTRACT

Derivatives of pyridopyrimidinone of the following formulae:

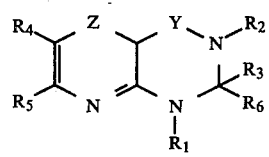

wherein
Y is C=S, C=O, SO$_2$, or CH$_2$;
Z is C—H, N, S or O;
R$_1$ is hydrogen, hydroxyl, halogen, lower alkyl or R$_3$;
R$_2$ is hydrogen, aliphatic hydrocarbon, substituted aliphatic hydrocarbon or carbocyclic aryl-aliphatic hydrocarbon, wherein the substituent of the aliphatic hydrocarbon may be hydroxyl, halogen, alkoxy, carboxylic acid ester, or lower alkyl amine;

R$_3$ is

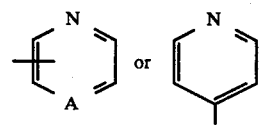

wherein A is carbon, nitrogen, oxygen, or sulfur;
R$_6$ is hydrogen, aliphatic hydrocarbon, substituted aliphatic hydrocarbon, aryl, substituted aryl, substituted carbocyclic aryl, carbocyclic aryl-lower aliphatic hydrocarbon, heterocyclic moiety, substituted heterocyclic moiety, heterocyclic aryl or heterocyclic aryl-lower aliphatic hydrocarbon,

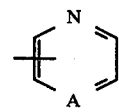

where A is carbon, nitrogen, oxygen or sulfur,

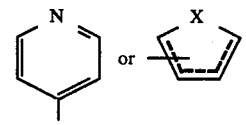

having 0, 1 or 2 double bonds where X is N, O or S;
wherein the substituent group may be hydroxyl, halogen, nitro, lower alkyl, alkoxy, carboxylic acid ester, lower alkyl amine, or sulfamoyl;
and R$_4$ and R$_5$ may by lower alkyl, substituted aromatic, halogen or hydrogen.

These compounds are useful for treating conditions associated with excess fluid retention and excess electrolyte retention.

3 Claims, No Drawings

PYRIDOPYRIMIDINONE DERIVATIVES

BACKGROUND OF THE INVENTION

Recent work by Osselaere and Lapiere showed that some derivatives of 4-oxo-3,4-dihyropyrido[2,3d-]pyrimidine had diuretic activity. (Eur. J. Med. Chem., 9:310 (1974); Eur. J. Med. Chem., 9:305 (1974)). They examined a series consisting of pyridyl and substituted phenyl groups attached at the 2 position on the pyrimidine ring. The most effective was 4-oxo-2-(3-pyridyl)-3,4-dihydropyrido[2,3d]pyrimidine (I, R=3-pyridyl).

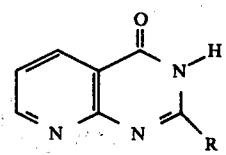

Osselaere and Lapiere, however, did not examine heterocyclic derivatives other than the pyridyl group.

Many investigators have studied the relationship between structure and diuretic activity for the many known diuretic compounds. See, for example, the work of Jackman, et al., J. Pharm. Pharmacol., 14:679 (1962); Siedel, et al., Chem. Ber., 99:328 (1966); Sturm, et al., Chem. Ber., 99:328 (1966); Feit, et al., J. Med. Chem. 13:1071 (1970) and Feit, et al., J. Med. Chem., 17:572 (1974), and in particular the discussions of furosemide, one of the most successful diuretics, and other aryl sulfonamides. It appears that the furyl moiety of these aryl sulfonamide compounds is important for diuretic activity. Other diuretic compounds somewhat related structurally to furosemide also have a furyl moiety. See, for example, U.S. Pat. Nos. 3,001,994; 3,058,882; 3,163,644; 3,839,321; and 4,064,239.

It is further known that chlorothiazide (II), a known diuretic, may be modified by reduction of the 1,2 double bond in the heterocyclic ring to form hydrochlorothiazide (III), having increased diuretic activity. (Osol, Ed., Remington's Pharmaceutical Science, 15th Ed., Mack Publ. Co., Easton, Pa., (1975), p. 868).

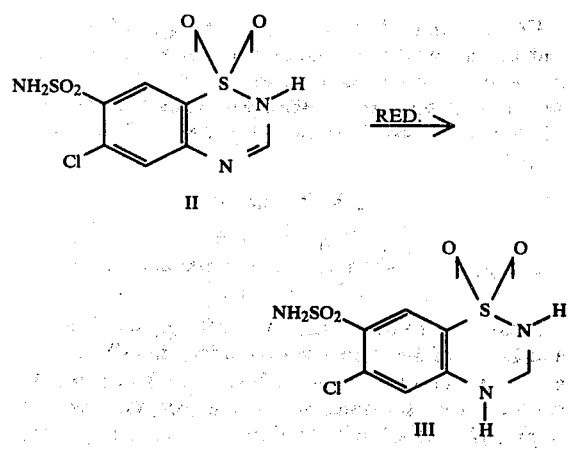

The present invention is an extension of this structure-activity work in that it combines teachings from various divergent areas of the diuretic art to arrive at novel compounds having exellent diuretic activity without causing potassium ion depletion and having low toxicity.

East German Pat. No. 73039 (Kretzschmar, et al.) discloses compounds of the formula:

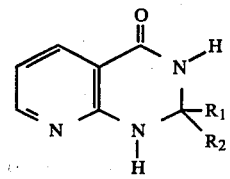

wherein $R_1$ is hydrogen or lower alkyl having 1-5 carbon atoms (straight or branched) and $R_2$ is lower alkyl having 1-5 carbon atoms (straight or branched) or aralkyl, aralkylidene or aryl, wherein the ring may be substituted with halogen, alkoxy, hydroxy, nitro, or tertiary amino. The compounds are disclosed as antitumor agents.

OBJECTS OF THE INVENTION

It is an object of the present invention to provide novel compounds having diuretic activity.

It is another object of the present invention provide novel compounds exhibiting diuretic activity and low toxicity while not causing potassium ion depletion.

It is still another object to provide methods of preparing the novel compounds of the invention.

Yet another object of this invention is to provide methods for increasing urinary output of animals and humans by administration, either orally, intravenously, rectally, etc., of the compounds and compositions of the invention.

DETAILED DESCRIPTION OF THE INVENTION

The novel compounds of the invention include compounds of the formulae:

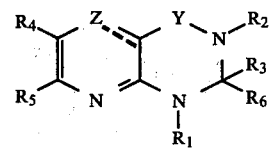

wherein
Y is C=S, C=O, SO$_2$, or CH$_2$;
Z is C—H, N, S or O;
$R_1$ is hydrogen, hydroxyl, halogen, lower alkyl or $R_3$;
$R_2$ is hydrogen, aliphatic hydrocarbon, substituted aliphatic hydrocarbon or carbocyclic aryl-aliphatic hydrocarbon, wherein the substituent of the aliphatic hydrocarbon may be hydroxyl, halogen, alkoxy, carboxylic acid ester, or lower alkyl amine;
$R_3$ is

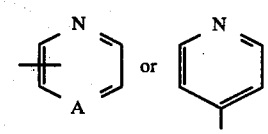

wherein A is carbon, nitrogen, oxygen, or sulfur;
$R_6$ is hydrogen, aliphatic hydrocarbon, substituted aliphatic hydrocarbon, aryl, substituted aryl, substituted carbocyclic aryl, carbocyclic aryl-lower aliphatic hydrocarbon, heterocyclic moiety, substituted heterocyclic moiety, heterocyclic aryl or heterocyclic aryl-lower aliphatic hydrocarbon,

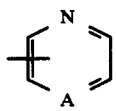

where A is carbon, nitrogen, oxygen or sulfur,

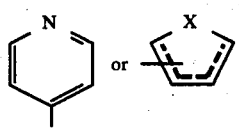

having 0, 1 or 2 double bonds where X is N, O or S; wherein the substituent group may be hydroxyl, halogen, nitro, lower alkyl, alkoxy, carboxylic acid ester, lower alkyl amine, or sulfamoyl; and $R_4$ and $R_5$ may be lower alkyl, substituted aromatic, halogen or hydrogen.

PREPARATIVE PROCEDURES

The 1,2-dihydro compounds of the invention were prepared by the condensation of the appropriate aldehyde with aminonicotinamide (VI, Procedure I). 2-(3-Pyridyl)-3-methyl-pyrido[2,3d]pyrimidin-4-one-1,2-dihyro (XII) was prepared in several steps starting from methyl amine and ethyl-2-amino-3-nicotinate (V, Procedure II).

In general the synthetic methods were modifications of Osselaere and Lapiere's procedures (cited above), and are not claimed as part of the present invention.

Procedure I

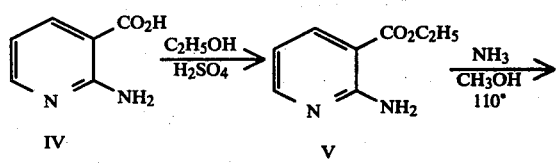

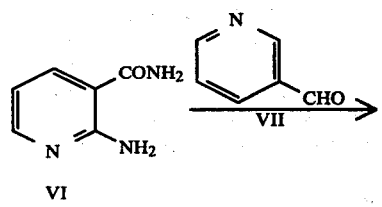

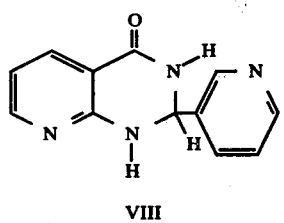

Procedure II

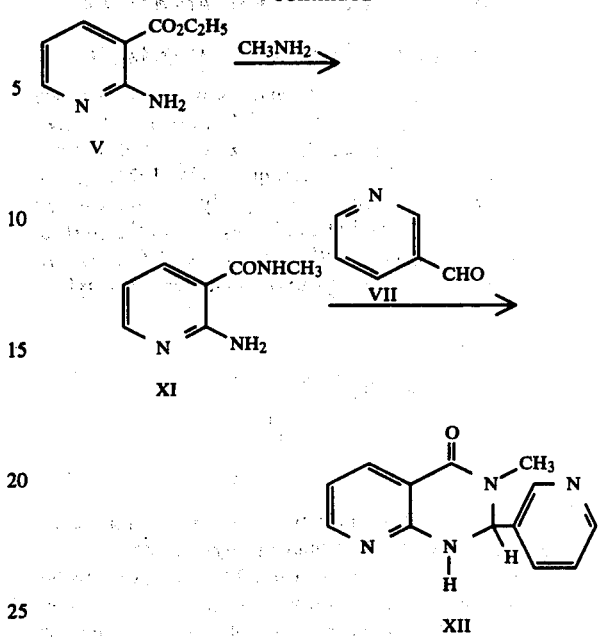

PROCEDURE I

EXAMPLE Ia

Preparation of ethyl-2-amino-3-nicotinate (V).

A Solution of 2-aminonicotinic acid (IV, 10.4 g., 0.075 moles) in 100 ml. of absolute ethanol containing 12.6 ml. of concentrated sulfuric acid was refluxed for 48 hours. The reaction mixture was concentrated to about 30 ml. on a rotary evaporator. The solution was then poured onto about 500 ml. of crushed ice and neutralized with sodium bicarbonate. The solution was extracted with chloroform, and then the chloroform was removed on the rotary evaporator. The solid was recrystallized from cylcohexane to give 8.75 g. (70% yield), melting point (m.p.) 93°–94.5°.

EXAMPLE Ib

Preparation of 2-amino-3-nicotinamide (VI)

Ethyl-2-amino-3-nicotinate (V, 6.0 g., 0.036 moles) and 150 ml. of dry methanol saturated with anhydrous ammonia were heated in an autoclave at 110°–115° for 48 hours. After concentrating and recrystallizing from ethanol 2.2 g. (45% yield), m.p. 194°–197° were obtained.

EXAMPLE Ic

Preparation of 2-(3-pyridyl)-3H-pyrido-[2,3d]pyrimidin-4-one-1,2-dihydro (VIII)

2-Amino-3-nicotinamide (VI, 2.95 g., 0.022 moles) and 22 ml. of 3-pyridyl carboxylaldehyde (VII) and 0.4 g. of zinc chloride were refluxed for 3 minutes. On cooling a solid separated which was recrystallized from isopropyl alcohol with carbon to give 2.6 g. (46% yield), m.p. 241°–243° C.

Analogous procedures can be used for the preparation of 2-(pyrazine)-3H-pyrido[2,3d]pyrimidin-4-one-1,2-dihydro (IX) and 2-(4-pyridyl)-3H-pyrido[2,3d]pyrimidin-4-one-1,2-dihydro (X).

EXAMPLE Id

Preparation of 1,4,5,7-tetraaza-8-oxo-5,6-dihydro-5-(3-pyridyl)naphthalene

A mixture of 160 ml. of methanol saturated with ammonia and 9.8 g. of 3-aminopyrazine-2-carboxylic acid benzyl ester was warmed to 50°. At this point the organic material dissolved and the reaction mixture was heated to 90° for 3 hours. After this time a solid had separated which was collected by filtration. The product, 3-aminopyrazine-2-carboxylamide (5.8 g., m.p. 232°–235°), was used without purification. To this was added 5 ml. of 3-pyridylcarboxylaldehyde and the mixture was refluxed for 3 minutes. After setting overnight, a solid separated which was recrystallized from ethanol.

When only limited quantities of the aldehyde are available or when the aldehyde is a solid then a solvent such as diethylene glycol dimethyl ether can be used. The reflux time is increased and when the reaction mixture solidified the reaction was stopped and worked up in the usual way.

PROCEDURE II

EXAMPLE II

Preparation of 2-(3-pyridyl)-3-methyl-pyrido[2,3d]pyrimidin-4-one-1,2-dihydro (XII)

Ethyl-2-amino-3-nicotinamide (V, 3.0 g. 0.018 moles) and 60 ml. of 40% aqueous methylamine were heated in an autoclave for 4 hours at 90°. The solvent was then removed under vacuum. Thin layer chromatography showed only one product (XI). 3-Pyridylcarboxylaldehyde (VII, 20 ml.) and 0.45 g. of zinc chloride was added and the solution refluxed for 3–4 minutes. After cooling 50 ml. of diethyl ether was added and a dark solid separated, which was recrystallized from isopropyl alcohol with carbon to give 1.5 g. (31% yield), m.p. 178°–179°.

BIOLOGICAL TESTS

EXAMPLE III

Diuretic Activity

The procedure used to obtain the $ED_{200}$ (the dose giving a 100% increase in urinary output over that of the control) was a modification of the method of Lipschitz, et al. (J. Pharmacol., 79:97 (1943)). This modified procedure is as follows: all animals were fasted for eighteen hours prior to administration of the test compound, but received water ad lib. All dosages were administered with the aid of an oral dosing needle.

Immediately after dosing, the animals were placed in metabolism cages designed to separate the urine and feces. The urine was then collected in plastic bottles for five hours after dosing. During this five hour interval, no feed or water was available for the test animals. At the end of the five hour period, the animals were removed from the metabolism cages. At this time an effort to force the animals to expel any urine remaining in their bladders was accomplished by pulling at the base of their tails.

Twenty-seven groups of eight male rats of Sprague-Dawley descent were used for this study. The drug vehicle (5% acacia-isotonic saline) was tested as the control and furosemide was tested for comparison with the test compounds.

Acute Oral Toxicity

Mice of Swiss-Webster descent were used. All animals were fasted overnight prior to treatment. Water was available prior to and during the study on an ad lib basis. Food was available ad lib after dosing. Food used was Wayne Lab-Blox. All test substances were suspended in 5% acacia immediately prior to administration. An oral dosing needle was used to administer the dosages. Each dosage group consisted of five male and five female animals. All animals were observed for death and/or toxic symptoms one-half, one, four, and twenty-four hours after treatment, and then daily for an additional thirteen days. $LD_{50}$ values were determined by standard methods.

SUMMARY OF RESULTS

A summary of the biological activity of two compounds of the invention, 2-(3-pyridyl)-3-methyl-pyrido[2,3d]pyrimidin-4-one-1,2-dihydro (XII) and 2-(3-pyridyl)-3H-pyrido-[2,3d]pyrimidin-4-one-1,2-dihydro (VIII), and furosemide is presented in Table I.

TABLE I

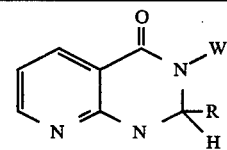

| Compound | W | R | $ED_{200}^a$ | $LD_{50}^b$ | Synthesis Procedure |
|---|---|---|---|---|---|
| VIII | H | 3-pyridyl | <25 | N.D. | I |
| XII | CH$_3$ | 3-pyridyl | <25 | N.D. | II |
| Furosemide | — | — | 24 | 900–1200 | — |

[a]Diuretic activity, mg./kg.
[b]Toxicity, mg./kg.
[c]Not Determined

EXAMPLE IV 2-(3-Pyridyl)-3H-pyrido[2,3d]pyrimidin-4-one-1,2-dihydro (VIII) was evaluated for diuretic activity in male Sprague-Dawley rats (190–235 g.) which were fasted and deprived of water for 18 hours prior to dosing. The activity was assessed on four separate occasions; the initial screening was performed at the 25 mg./kg. (p.o.) dose-level while subsequent studies included doses ranging from 1 to 81 mg./kg. (p.o.). In each case, additional groups of rats were given hydrochlorothiazide at dose-levels at which known diuretic activity could be elicited.

On the morning of the experiment groups of animals (8 rats per group) were administered with either 2-(3-pyridyl)-3H-pyrido[2,3d]pyrimidin-4-one-1,2-dihydro (VIII), hydrochlorothiazide or physiological saline alone. Various concentrations of the test substances suspended in saline were utilized so that each animal in the test received a final saline volume of 25 ml./kg. Immediately after dosing, pairs of rats were placed in metabolism cages. After 5 hours the rats were removed from their cages and residual bladder urine was expressed by tail pulling. The analysis for sodium and potassium was determined by a flame photometer and chloride content was obtained with a colorimeter. The results were calculated to show 5-hour volume, sodium and chloride excretion as percent of the original load dosed.

2-(3-Pyridyl)pyrido[2,3d]pyrimidin-4-one-1,2-dihydro (VIII) was administered as a suspension in saline. Hydrochlorothiazide, while partially solubilized, was also administered in suspended form.

The effect of 2-(3-pyridyl)-3H-pyrido[2,3d]pyrimidin-4-one-1,2-dihydro (VIII) and hydrochlorothiazide on urine output and urine Na+, K+ and CL− concentration are shown in Table II.

The results from each of the four studies performed did not differ appreciably when similar treatments with the same substances are compared. However, the activity profile of both compounds were found to be quite different. Hydrochlorothiazide increased urine output at doses ranging from 1 to 9 mg./kg.; no significant diuretic activity was detected when 2-(3-pyridyl)-3H-pyrido[2,3d]pyrimidin-4-one-1,2-dihydro (VIII) was given at similar doses. Significant diuretic activity was first noted when 2-(3-pyridyl)-3H-pyrido[2,3d]pyrimidin-4-one-1,2-dihydro (VIII) was miximal around 25 mg./kg. and it was more effective than hydrochlorothiazide at this dose-level; however, the excretion level of electrolytes (NA[30], K+ and Cl[31]) for both compounds was not dissimilar. The highest dose of 2-(3-pyridyl)-3H-pyrido-[2,3d]pyrimidin-4-one-1,2-dihydro (VIII) tested (81 mg./kg.) was slightly less effective in eliciting diuresis than the latter dose but K+ excretion was similar to that produced by the saline control.

These studies clearly indicate that 2-(3-pyridyl)-3H-pyrido[2,3d]pyrimidin-4-one-1,2-dihydro (VIII) possesses diuretic activity after oral administration. Hydrochlorothiazide produces significant diuresis at lower doses than 2-(3-pyridyl)-3H-pyrido-[2,3d]pyrimidin-4-one1,2dihydro (VIII). However, at higher doses (25 mg./kg. and greater) 2-(3-pyridyl)-3H-pyrido[2,3d]pyrimidin-4-one-1,2-dihydro (VIII) is more effective than hydrochlorothiazide.

A desirable property of new diuretic drugs is the ability to affect urine output without casuing potassium ion depletion. Like hydrochlorothiazide, 2-(3-pyridyl)-3H-pyrido-[2,3d]pyrimidine-4-one-1,2-dihydro (VIII) causes potassium ion excretion at effective diuretic doses although at the highest dose examined (81 mg./kg.) potassium ion excretion was not significantly different from the saline control. An explantion for this observation is not readily available. However, it seems likely that at high doses 2-(3-pryidyl)-3H-pyrido[2,3d-]pyrimidin-4-one-1,2-dihydro (VIII) exerts a diuretic effect via a mechanism different from that produced by hydrochlorothiazide. Consequently these data indicate that 2-(3-pyridyl)-3H-pyrido[2,3d]pyrimidin-4-one-1,2-dihydro (VIII), unlike hydrochlorothiazide, possesses two different mechanisms of action.

EXAMPLE V

Studies with 2(3-pyridyl)-3H-pyrido[2,3d]pyrimidin-4-one-1,2-dihydro (VIII), 2-(3-pyridyl)3-methylpyrido[2,3d]-yrimidin-4-one-1,2-dihydro (XII) and hydrochlorothiazide were performed essentially as in Example IV. Groups of eight rats were used, and immediately after dosing, pairs of rats were placed in a metabolism cage. The volume of urine collected at two and five hours after dosing was measured. In addition, the five-hour urine was analyzed for electrolyte content. The results for volume, sodium and chlorine excretion are expressed as percent of original load.

In an initial experiment (No. 1 of Table III) all three compounds increased urine output at both two and five hours. The potencies of compound VIII and hydrochlorothiazide were approximately the same and were greater than that of compound XII. Each compound also increased sodium, potassium and chloride in excretion over the control (saline). Compound VIII was the most effective in increasing the Na+/K+ ratio.

2-(3-Pyridyl)-3H-pyrido[2,3d]pyrimidin-4-one-1,2-dihydro (VIII) was compared with hydrochlorothiazide in Experiment No. 2 of Table III. Again, favorable comparisons of diuretic activities were obtained.

TABLE II

Diuretic effects of 1,2Dihydro-2-(3-pyridyl)pyrido[2,3d]pyrimidin-4(h)-one (5 hr study).[a]

| Experiment No. | Test compound | Dose[b] mg/kg | Volume ml given | Volume ml excreted | Volume % excreted | Na+ Total mEq excreted | Na+ % excreted | Cl− Total mEq excreted | Cl− % excreted | F+ Total mEq excreted |
|---|---|---|---|---|---|---|---|---|---|---|
| 1 | Saline | — | 10.8 ± 0.2 | 6.0 ± 1.0 | 55.2 ± 8.9 | 0.91 ± 0.11 | 55.8 ± 6.6 | 1.05 ± 0.11 | 63.9 ± 6.1 | 0.41 ± 0.07 |
|  | Hydrochlorothiazode | 12 | 10.4 ± 0.2 | 16.0 ± 0.6[c] | 154.4 ± 6.8 | 2.45 ± 0.11[c] | 157.9 ± 8.0 | 2.80 ± 0.10[c] | 178.8 ± 7.2 | 0.64 ± 0.03[c] |
|  | 1,2Dihydro-2-(3-pyridyl)pyrido[2,3d]-pyrimidin-4(H)-one | 25 | 10.3 ± 0.1 | 21.0 ± 1.0[c] | 203.6 ± 10.4 | 2.45 ± 0.09[c] | 157.9 ± 6.6 | 2.78 ± 0.08[c] | 178.7 ± 5.8 | 0.64 ± 0.07[c] |
| 2 | Saline | — | 10.7 ± 0.4 | 6.4 ± 0.9 | 59.3 ± 6.9 | 0.94 ± 0.05 | 57.4 ± 2.9 | 1.07 ± 0.07 | 65.0 ± 3.5 | 0.31 ± 0.04 |
|  | Hydrochlorothiazide | 1 | 10.6 ± 0.1 | 10.9 ± 0.7[c] | 102.3 ± 6.3 | 1.73 ± 0.10[c] | 106.5 ± 5.9 | 2.07 ± 0.16[c] | 126.6 ± 9.0 | 0.42 ± 0.06 |
|  |  | 3 | 10.6 ± 0.2 | 13.2 ± 0.3[c] | 125.4 ± 3.9 | 2.15 ± 0.07[c] | 132.8 ± 3.7 | 2.47 ± 0.10[c] | 151.4 ± 4.8 | 0.48 ± 0.02[c] |
|  |  | 6 | 10.8 ± 0.1 | 14.6 ± 0.2[c] | 135.5 ± 3.2 | 2.31 ± 0.04[c] | 139.7 ± 3.7 | 2.79 ± 0.05[c] | 168.1 ± 4.6 | 0.58 ± 0.02[c] |
|  |  | 12 | 10.8 ± 0.2 | 16.1 ± 0.9[c] | 149.7 ± 5.5 | 2.37 ± 0.08[c] | 143.8 ± 3.6 | 2.75 ± 0.08[c] | 166.1 ± 4.3 | 0.62 ± 0.02[c] |
|  |  | 25 | 10.8 ± 0.1 | 15.8 ± 1.0[c] | 146.0 ± 7.9 | 2.47 ± 0.08[c] | 149.8 ± 3.4 | 2.76 ± 0.10[c] | 166.0 ± 4.5 | 0.56 ± 0.06[c] |
|  | 1,2Dihydro-2-(3-pyridyl)pyrido[2,3d]-pyrimidin-4(H)-one | 1 | 10.7 ± 0.1 | 6.6 ± 0.9 | 62.0 ± 8.3 | 0.97 ± 0.11 | 60.6 ± 6.8 | 1.14 ± 0.11 | 69.2 ± 7.0 | 0.45 ± 0.05[c] |
|  |  | 3 | 11.0 ± | 7.1 ± | 64.9 ± | 1.10 ± 0.04 | 65.2 ± | 1.22 ± 0.03 | 71.8± | 0.36 ± 0.03 |
|  |  | 6 | 11.1 ± 0.1 | 7.6 ± 0.6 | 68.9 ± 5.3 | 1.14 ± 0.12 | 67.6 ± 7.2 | 1.26 ± 0.10 | 74.0 ± 5.5 | 0.41 ± 0.01 |
|  |  | 12 | 10.9 ± 0.1 | 11.7 ± 1.6[c] | 107.0 ± 13.1 | 1.39 ± 0.10[c] | 83.4 ± 5.4 | 1.59 ± 0.14[c] | 94.4 ± 7.7 | 0.48 ± 0.08[c] |
|  |  | 25 | 10.7 ± 0.1 | 20.1 ± 1.9[c] | 187.7 ± 16.8 | 2.43 ± 0.14[c] | 148.7 ± 8.2 | 2.71 ± 0.17[c] | 165.0 ± 9.5 | 0.65 ± 0.02[c] |

TABLE II-continued
Diuretic effects of 1,2Dihydro-2-(3-pyridyl)pyrido[2,3d]pyrimidin-4(h)-one (5 hr study).[a]

| Experiment No. | Test compound | Dose[b] mg/kg | Volume ml given | Volume ml excreted | Volume % excreted | Na+ Total mEq excreted | Na+ % excreted | Cl− Total mEq excreted | Cl− % excreted | F+ Total mEq excreted |
|---|---|---|---|---|---|---|---|---|---|---|
| 3 | Saline | — | 10.7 ± 0.1 | 7.9 ± 0.4 | 73.4 ± 4.0 | 1.11 ± 0.06 | 68.6 ± 3.0 | 1.23 ± 0.05 | 75.0 ± 2.8 | 0.40 ± 0.06 |
|  | Hydrochlorothiazide | 1 | 10.9 ± 0.1 | 13.9 ± 1.4[c] | 126.8 ± 12.1 | 2.03 ± 0.2[c] | 122.7 ± 11.2 | 2.45 ± 0.19[c] | 145.3 ± 10.6 | 0.63 ± 0.11 |
|  |  | 3 | 10.8 ± 0.2 | 15.8 ± 0.9[c] | 146.6 ± 7.7 | 2.39 ± 0.11[c] | 147.6 ± 8.8 | 2.73 ± 0.06[c] | 165.4 ± 5.1 | 0.58 ± 0.05 |
|  |  | 9 | 10.8 ± 0.2 | 14.6 ± 1.0[c] | 135.2 ± 7.1 | 2.23 ± 0.09[c] | 136.8 ± 5.0 | 2.65 ± 0.12[c] | 159.0 ± 5.9 | 0.59 ± 0.06 |
|  |  | 27 | 10.7 ± 0.4 | 15.1 ± 1.0[c] | 140.7 ± 3.3 | 2.53 ± 0.31[c] | 154.8 ± 12.1 | 3.01 ± 0.42[c] | 180.0 ± 17.0 | 0.78 ± 0.30[c] |
|  | 1,2Dihydro-2-(3-pyridyl)pyrido[2,3d]-pyrimidin-4(H)-one | 3 | 10.3 ± 0.2 | 8.1 ± 0.5 | 78.9 ± 6.5 | 1.28 ± 0.10 | 82.8 ± 8.4 | 1.45 ± 0.09 | 91.8 ± 8.1 | 0.35 ± 0.04 |
|  |  | 9 | 10.9 ± 0.2 | 7.6 ± 0.4 | 69.5 ± 3.5 | 1.09 ± 0.03 | 66.5 ± 2.8 | 1.27 ± 0.07 | 76.0 ± 4.4 | 0.43 ± 0.04 |
|  |  | 27 | 10.8 ± 0.3 | 20.1 ± 1.9[c] | 187.1 ± 19.1 | 2.23 ± 0.24[c] | 137.5 ± 15.9 | 2.57 ± 0.24[c] | 155.4 ± 15.6 | 0.59 ± 0.06 |
|  |  | 81 | 10.5 ± 0.2 | 19.6 ± 0.8[c] | 185.9 ± 9.4 | 2.60 ± 0.13[c] | 163.1 ± 10.4 | 2.61 ± 0.11[c] | 160.6 ± 8.3 | 0.41 ± 0.06 |
| 4 | Saline | — | 10.6 ± 0.1 | 7.8 ± 1.2 | 72.8 ± 10.7 | 1.08 ± 0.13 | 66.2 ± 7.8 | 1.15 ± 0.13 | 70.7 ± 8.2 | 0.36 ± 0.06 |
|  | Hydrochlorothiazide | 25 | 10.4 ± 0.2 | 15.1 ± 0.6[c] | 145.1 ± 4.7 | 2.31 ± 0.06[c] | 145.0 ± 5.8 | 2.61 ± 0.10[c] | 163.9 ± 6.6 | 0.52 ± 0.03[c] |
|  | 1,2Dihydro-2-(3-pyridyl(pyrido[2,3d]-pyrimidin-4(H)-one | 27 | 10.6 ± 0.2 | 20.8 ± 1.3[c] | 195.9 ± 14.0 | 2.45 ± 0.21[c] | 150.8 ± 14.0 | 2.67 ± 0.21[c] | 164.2 ± 14.8 | 0.57 ± 0.04[c] |
|  |  | 81 | 10.6 ± 0.2 | 17.9 ± 0.6[c] | 169.5 ± 4.5 | 2.53 ± 0.08[c] | 157.0 ± 5.6 | 2.49 ± 0.08[c] | 154.4 ± 5.4 | 0.33 ± 0.04 |

[a]Mean values ± SEM of 2 rats per cage. Total of eight rats per group.
[b]Animals received 25 ml/kg saline p.o. in the presence or absence of drug.
[c]Significantly different (P 0.05) from saline control.

TABLE III
Diuretic effects of Compounds VIII, XII and hydrochlorothiazide in the rat.[a,b]

| Expt. | Compound | Oral Dose mg/kg | Volume ml Given | Volume ml Excreted 2 hr | Volume ml Excreted 5 hr | Volume % Excreted 2 hr | Volume % Excreted 5 hr | Na+ Total mEq Excreted | Na+ % Excreted | Cl− Total mEq Excreted | Cl− % Excreted | K+ Total mEq Excreted | Na+/K+ Ratio Excreted |
|---|---|---|---|---|---|---|---|---|---|---|---|---|---|
| 1 | Saline | — | 10.9 | 2.4 | 6.0 | 21.8 | 55.2 | 0.9 | 55.8 | 1.1 | 63.9 | 0.4 | 2.5 |
|  | VIII | 25 | 10.3 | 8.0 | 21.0 | 77.7 | 203.6 | 2.5 | 158.0 | 2.8 | 178.7 | 0.6 | 4.0 |
|  | XII | 25 | 10.5 | 4.6 | 12.2 | 43.8 | 116.2 | 1.8 | 111.4 | 1.8 | 115.9 | 0.8 | 2.3 |
|  | Hydrochlorothiazide | 12 | 10.4 | 7.9 | 16.0 | 75.8 | 154.4 | 2.5 | 157.0 | 2.8 | 178.8 | 0.6 | 3.9 |
| 2 | Saline | — | 10.7 | 2.5 | 7.9 | 23.5 | 73.8 | 1.1 | 68.6 | 1.2 | 75.0 | 0.4 | 2.8 |
|  | VIII | 3 | 10.4 | 4.4 | 8.1 | 65.4 | 78.9 | 1.4 | 87.7 | 1.6 | 97.6 | 0.4 | 3.8 |
|  | VIII | 9 | 10.9 | 3.0 | 7.6 | 27.8 | 69.9 | 1.1 | 66.5 | 1.3 | 76.0 | 0.4 | 2.6 |
|  | VIII | 27 | 10.8 | 10.4 | 20.1 | 96.9 | 187.1 | 2.2 | 137.5 | 2.6 | 155.4 | 0.6 | 3.8 |
|  | VIII | 81 | 10.6 | 6.0 | 19.6 | 57.0 | 185.9 | 2.6 | 163.1 | 2.6 | 160.6 | 0.4 | 6.8 |
|  | Hydrochlorothiazide | 1 | 10.9 | 7.8 | 13.9 | 70.8 | 126.8 | 2.0 | 122.7 | 2.5 | 145.3 | 0.6 | 3.4 |
|  | Hydrochlorothiazide | 3 | 10.8 | 8.1 | 15.8 | 75.7 | 146.6 | 2.4 | 147.6 | 2.7 | 165.4 | 0.6 | 4.3 |
|  | Hydrochlorothiazide | 9 | 10.8 | 7.5 | 14.6 | 68.9 | 135.2 | 2.2 | 136.8 | 2.7 | 159.0 | 0.6 | 3.9 |
|  | Hydrochlorothiazide | 27 | 10.7 | 8.4 | 15.1 | 93.2 | 140.6 | 2.5 | 154.8 | 3.0 | 180.0 | 0.8 | 4.0 |

[a]Animals received 25 ml/kg saline in the absence or presence of drug.
[b]Mean values of 2 rats per cage (n = 8)

CLINICAL ADMINISTRATION

As demonstrated above, the new compounds of the invention are suitable as diuretic agents, and in consequence are particularly useful for the clinical treatment of edemas and other conditions associated with excess fluid retention and excess electrolyte retention. The novel compounds are active in their free form as well as in the form of their physiologically acceptable metal salts in oral as well as in parenteral administration. Therefore, they can be used as such or in admixture with suitable pharmaceutically acceptable carriers in solid or liquid form, for example, water, vegetable oils, starch, lactose, magnesium stearate, terra alba, talc, stearic acid, pectin, talcum or with auxiliary agents, for example, stabilizers, preserving, wetting or emulsifying agents. The products can be compounded in the form of tablets, dragees, capsules, solutions, suspensions or emulsions. With particular advantage the compounds are orally applied in the form of tablets or dragees having dosages in the range of 5 to 500 mg. Advantageously, a dose will be administered from one to four times daily.

The compounds of the invention are also capable of being administered in amounts effective for diuretic therapy by dispensing or dissolving the solid compound in any convenient injectable vehicle.

The total daily dose regimen, for any of the above-listed routes of administration, is from about 5 mg. to about 1000 mg., preferably about 10 mg. to about 750 mg.

EXAMPLE VI

Patients are given 80 mg. of 2-(3-pyridyl)-3H-pyrido[2,3d]pyrimidin-4-one-1,2-dihydro (VIII). Diuresis commences within one hour, the peak effect occuring within the first or second hour; the duration of the diuretic effect is 6 to 8 hours.

Depending on the individual patient's response, a second dose is administered 6 to 8 hours after the initial dose.

While the above specification describes the preparation of certain illustrative compounds of the invention and certain specific dosage forms suitable for administering the compounds in human therapy, it is to be understood that the invention is not to be limited by these examples or by the specific reaction conditions described for the preparation of the compounds or by the specific ingredients in the pharmaceutical preparations, but is understood to embrace variations and modifications falling within the scope of the appended claims.

What is claimed is:
1. 2-(3-Pyridyl)-3H-pyrido[2,3d]pyrimidin-4-one-1,2-dihydro.
2. 2-(4-Pyridyl)-3H-pyrido[2,3d]pyrimidin-4-one-1,2-dihydro.
3. 2(3-Pyridyl)-3-methyl-pyrido[2,3d]pyrimidin-4-one-1,2-dihydro.

* * * * *